United States Patent
Roe et al.

(10) Patent No.: US 6,988,996 B2
(45) Date of Patent: Jan. 24, 2006

(54) TEST MEDIA CASSETTE FOR BODILY FLUID TESTING DEVICE

(75) Inventors: Jeffrey N. Roe, San Ramon, CA (US); Steven N. Roe, San Mateo, CA (US)

(73) Assignee: Roche Diagnostics Operatons, Inc., Indianapolis, IN (US)

( * ) Notice: Subject to any disclaimer, the term of this patent is extended or adjusted under 35 U.S.C. 154(b) by 397 days.

(21) Appl. No.: 10/164,828

(22) Filed: Jun. 7, 2002

(65) Prior Publication Data

US 2002/0188224 A1 Dec. 12, 2002

Related U.S. Application Data

(60) Provisional application No. 60/296,989, filed on Jun. 8, 2001.

(51) Int. Cl.
  A61B 5/00    (2006.01)
  B65D 81/00   (2006.01)

(52) U.S. Cl. ...................................... 600/584
(58) Field of Classification Search ............... 600/584, 600/583, 586, 556, 573, 575; 204/222, 400, 204/403.08, 403.1, 409, 412, 415; 257/414; 435/817; 436/806, 170, 44, 165; 222/144, 222/166; 144/100, 284; 414/421; 422/66, 422/67, 56, 102, 104, 58, 62, 944; 356/440; 205/778, 793

See application file for complete search history.

(56) References Cited

U.S. PATENT DOCUMENTS

| | | |
|---|---|---|
| 2,714,890 A | 8/1955 | Vang |
| 3,086,288 A | 4/1963 | Balamuth et al. |
| 3,208,452 A | 9/1965 | Stern |
| 3,260,413 A * | 7/1966 | Natelson ............... 222/144 |
| 3,298,789 A | 1/1967 | Mast ..................... 23/253 |
| 3,526,480 A * | 9/1970 | Findl et al. |
| 3,620,678 A * | 11/1971 | Guigan et al. |
| 3,673,475 A | 6/1972 | Britton, Jr. |
| 3,786,510 A * | 1/1974 | Hodges |
| 3,802,842 A | 4/1974 | Lange et al. ............ 23/253 |
| 3,832,776 A | 9/1974 | Sawyer |
| 4,061,468 A | 12/1977 | Lange et al. ............ 23/253 |
| 4,077,406 A | 3/1978 | Sandhage et al. |
| 4,154,228 A | 5/1979 | Feldstein et al. |
| 4,203,446 A | 5/1980 | Hofert et al. |
| 4,218,421 A | 8/1980 | Mack, Jr. et al. |

(Continued)

FOREIGN PATENT DOCUMENTS

| | | |
|---|---|---|
| DE | 4234553 A1 | 10/1992 |
| DE | 19819407 A1 | 4/1998 |
| DE | 198 49 539 A1 | 5/2000 |

(Continued)

*Primary Examiner*—Max F. Hindenburg
*Assistant Examiner*—Brian Szmal
(74) *Attorney, Agent, or Firm*—Woodard, Emhardt, Moriarty McNett & Henry LLP

(57) ABSTRACT

A bodily fluid sampling device includes a piercing device and a sensor enclosed in a housing. A cassette, which contains test media, is positioned proximal to the sensor so that the sensor is able to analyze a bodily fluid sample collected on the test media. The cassette includes a supply portion from which unused test media is supplied and a storage portion in which contaminated test media is stored after exposure to the bodily fluid. The cassette is adapted to collect a series of bodily fluid samples without requiring disposal of the test media.

29 Claims, 8 Drawing Sheets

U.S. PATENT DOCUMENTS

| | | | |
|---|---|---|---|
| 4,223,674 A | 9/1980 | Fluent et al. | |
| 4,230,118 A | 10/1980 | Holman et al. | |
| 4,328,184 A * | 5/1982 | Kondo | |
| 4,356,826 A | 11/1982 | Kubota | |
| 4,449,529 A | 5/1984 | Burns et al. | |
| 4,462,405 A | 7/1984 | Ehrlich | |
| 4,490,465 A | 12/1984 | Limbach et al. | 435/14 |
| 4,518,384 A | 5/1985 | Tarello et al. | |
| 4,535,773 A | 8/1985 | Yoon | |
| 4,553,541 A | 11/1985 | Burns et al. | |
| 4,627,445 A | 12/1986 | Garcia et al. | |
| 4,637,403 A | 1/1987 | Garcia | 128/770 |
| 4,653,513 A | 3/1987 | Dombrowski | |
| 4,750,489 A | 6/1988 | Berkman et al. | |
| 4,787,398 A | 11/1988 | Garcia et al. | |
| 4,794,926 A | 1/1989 | Munsch et al. | |
| 4,823,806 A | 4/1989 | Bajada | |
| 4,883,642 A * | 11/1989 | Bisconte | |
| 4,911,794 A * | 3/1990 | Parce et al. | 205/778 |
| 4,924,879 A | 5/1990 | O'Brien | 128/770 |
| 4,994,167 A | 2/1991 | Shults et al. | 204/403 |
| 4,995,402 A | 2/1991 | Smith et al. | |
| 5,029,583 A | 7/1991 | Meserol et al. | |
| 5,035,704 A | 7/1991 | Lambert et al. | |
| 5,047,044 A | 9/1991 | Smith et al. | |
| 5,053,199 A | 10/1991 | Keiser et al. | 422/68.1 |
| 5,077,010 A * | 12/1991 | Ishizaka et al. | 422/56 |
| 5,096,828 A * | 3/1992 | Ishizaka et al. | 436/44 |
| 5,097,810 A | 3/1992 | Fishman et al. | |
| 5,145,565 A | 9/1992 | Kater et al. | |
| 5,152,775 A | 10/1992 | Ruppert | |
| 5,178,835 A * | 1/1993 | Uekusa et al. | |
| 5,188,118 A | 2/1993 | Terwilliger | |
| 5,189,751 A | 3/1993 | Giuliani et al. | |
| 5,206,147 A | 4/1993 | Hoenes | |
| 5,222,504 A | 6/1993 | Solomon | |
| 5,228,972 A | 7/1993 | Osaka et al. | |
| 5,240,860 A | 8/1993 | Hoenes et al. | |
| 5,279,294 A | 1/1994 | Anderson et al. | 128/633 |
| 5,304,468 A | 4/1994 | Phillips et al. | 435/14 |
| 5,307,263 A | 4/1994 | Brown | 364/413.09 |
| 5,320,808 A | 6/1994 | Holen et al. | |
| 5,334,508 A | 8/1994 | Hoenes | |
| 5,366,609 A | 11/1994 | White et al. | 204/403 |
| 5,368,047 A | 11/1994 | Suzuki et al. | |
| 5,382,523 A | 1/1995 | Hoenes et al. | |
| 5,415,169 A | 5/1995 | Siczek et al. | |
| 5,418,142 A | 5/1995 | Kiser et al. | 435/14 |
| 5,423,847 A | 6/1995 | Strong et al. | |
| 5,451,350 A | 9/1995 | Macho et al. | 264/442 |
| 5,472,427 A | 12/1995 | Rammler | |
| 5,474,084 A | 12/1995 | Cunniff | |
| 5,510,266 A | 4/1996 | Bonner et al. | |
| 5,514,152 A | 5/1996 | Smith | |
| 5,515,170 A | 5/1996 | Matzinger et al. | 356/423 |
| 5,521,060 A | 5/1996 | Hoenes et al. | |
| 5,522,255 A | 6/1996 | Neel et al. | 73/64.43 |
| 5,529,074 A | 6/1996 | Greenfield | |
| 5,575,403 A | 11/1996 | Charlton et al. | |
| 5,580,794 A | 12/1996 | Allen et al. | 436/169 |
| 5,630,986 A | 5/1997 | Charlton et al. | |
| 5,632,410 A | 5/1997 | Moulton et al. | |
| 5,660,791 A | 8/1997 | Brenneman et al. | |
| 5,679,311 A * | 10/1997 | Harttig et al. | |
| 5,686,829 A | 11/1997 | Girault | |
| 5,700,695 A | 12/1997 | Yassinzadeh et al. | |
| 5,714,390 A | 2/1998 | Hallowitz et al. | |
| 5,720,924 A | 2/1998 | Eikmeier et al. | |
| 5,738,244 A | 4/1998 | Charlton et al. | |
| RE35,803 E | 5/1998 | Lange et al. | 606/182 |
| 5,758,643 A | 6/1998 | Wong et al. | |
| 5,776,157 A | 7/1998 | Thorne et al. | |
| 5,776,719 A | 7/1998 | Douglas et al. | 435/28 |
| 5,788,651 A | 8/1998 | Weilandt | |
| 5,800,781 A | 9/1998 | Gavin et al. | |
| 5,801,057 A | 9/1998 | Smart et al. | |
| 5,810,199 A | 9/1998 | Charlton et al. | |
| 5,823,973 A | 10/1998 | Racchini et al. | |
| 5,824,491 A | 10/1998 | Priest et al. | 435/28 |
| 5,830,219 A | 11/1998 | Bird et al. | |
| 5,846,490 A | 12/1998 | Yokota et al. | |
| 5,854,074 A | 12/1998 | Charlton et al. | |
| 5,855,801 A | 1/1999 | Lin et al. | |
| 5,857,983 A | 1/1999 | Douglas et al. | 600/538 |
| 5,863,800 A | 1/1999 | Eikmeier et al. | |
| 5,871,494 A | 2/1999 | Simons et al. | |
| 5,879,311 A | 3/1999 | Duchon et al. | 600/583 |
| 5,880,829 A | 3/1999 | Kauhaniemi et al. | |
| 5,885,211 A | 3/1999 | Eppstein et al. | |
| 5,891,053 A | 4/1999 | Sesekura | |
| 5,916,229 A | 6/1999 | Evans | |
| 5,935,075 A | 8/1999 | Casscells et al. | |
| 5,938,679 A | 8/1999 | Freeman et al. | |
| 5,951,492 A | 9/1999 | Douglas et al. | 600/583 |
| 5,951,493 A | 9/1999 | Douglas et al. | 600/583 |
| 5,951,582 A | 9/1999 | Thorne et al. | |
| 5,962,215 A | 10/1999 | Douglas et al. | 435/4 |
| 5,964,718 A | 10/1999 | Duchon et al. | 600/583 |
| 5,968,063 A | 10/1999 | Chu et al. | |
| 5,971,941 A | 10/1999 | Simons et al. | |
| 5,997,561 A | 12/1999 | Bocker et al. | |
| 5,997,817 A * | 12/1999 | Crismore et al. | |
| 6,022,324 A | 2/2000 | Skinner | |
| 6,027,459 A | 2/2000 | Shain et al. | |
| 6,036,919 A | 3/2000 | Thym et al. | |
| 6,036,924 A | 3/2000 | Simons et al. | |
| 6,048,352 A | 4/2000 | Douglas et al. | 606/181 |
| 6,071,294 A | 6/2000 | Simons et al. | |
| 6,086,545 A | 7/2000 | Roe et al. | 600/570 |
| 6,090,078 A | 7/2000 | Erskine | |
| 6,093,156 A | 7/2000 | Cunningham et al. | |
| 6,099,484 A | 8/2000 | Douglas et al. | 600/583 |
| 6,117,630 A | 9/2000 | Reber et al. | |
| 6,120,462 A | 9/2000 | Hibner et al. | |
| 6,132,449 A | 10/2000 | Lum et al. | |
| 6,136,013 A | 10/2000 | Marshall et al. | |
| 6,139,562 A | 10/2000 | Mauze et al. | |
| 6,143,164 A | 11/2000 | Heller et al. | |
| 6,152,942 A | 11/2000 | Brenneman et al. | |
| 6,155,992 A | 12/2000 | Henning et al. | |
| 6,156,051 A | 12/2000 | Schraga | |
| 6,159,424 A | 12/2000 | Kauhaniemi et al. | |
| 6,171,325 B1 | 1/2001 | Mauze et al. | |
| 6,176,865 B1 | 1/2001 | Mauze et al. | |
| 6,183,489 B1 | 2/2001 | Douglas et al. | 606/181 |
| 6,193,673 B1 | 2/2001 | Viola et al. | |
| 6,203,504 B1 | 3/2001 | Latterell et al. | |
| 6,206,841 B1 | 3/2001 | Cunningham et al. | |
| 6,210,420 B1 | 4/2001 | Mauze et al. | |
| 6,210,421 B1 | 4/2001 | Bocker et al. | |
| 6,228,100 B1 | 5/2001 | Schraga | |
| 6,231,531 B1 | 5/2001 | Lum et al. | |
| 6,261,241 B1 | 7/2001 | Burbank et al. | |
| 6,261,245 B1 | 7/2001 | Kawai et al. | |
| D448,294 S | 9/2001 | Alscher et al. | |
| 6,283,926 B1 | 9/2001 | Cunningham et al. | |
| 6,285,454 B1 | 9/2001 | Douglas et al. | |
| 6,306,104 B1 | 10/2001 | Cunningham et al. | |
| 6,306,152 B1 | 10/2001 | Verdonk et al. | |
| 6,315,738 B1 | 11/2001 | Nishikawa et al. | |

| | | |
|---|---|---|
| 6,319,210 B1 | 11/2001 | Douglas et al. |
| 6,332,871 B1 | 12/2001 | Douglas et al. .............. 600/583 |
| 6,352,514 B1 | 3/2002 | Douglas et al. |
| 6,364,889 B1 | 4/2002 | Kheiri et al. |
| 6,364,890 B1 | 4/2002 | Lum et al. |
| 6,375,627 B1 | 4/2002 | Mauze et al. |
| 6,379,317 B1 | 4/2002 | Kintzig et al. |
| 6,379,969 B1 | 4/2002 | Mauze et al. |
| 6,391,005 B1 | 5/2002 | Lum et al. |
| 6,402,701 B1 | 6/2002 | Kaplan et al. |
| 6,402,704 B1 | 6/2002 | McMorrow |
| 6,409,740 B1 | 6/2002 | Kuhr et al. |
| 6,461,496 B1 | 10/2002 | Feldman et al. |
| 6,472,220 B1 | 10/2002 | Simons et al. |
| 6,485,439 B1 | 11/2002 | Roe et al. |
| 6,488,891 B2 | 12/2002 | Mason et al. |
| 6,491,709 B2 | 12/2002 | Sharma et al. |
| 6,497,845 B1 | 12/2002 | Sacherer |
| 6,503,210 B1 | 1/2003 | Hirao et al. |
| 6,506,575 B1 | 1/2003 | Knappe et al. |
| 6,530,892 B1 | 3/2003 | Kelly |
| 6,887,709 B2 * | 5/2005 | Leong |
| 2001/0031931 A1 | 10/2001 | Cunningham et al. |
| 2002/0002344 A1 | 1/2002 | Douglas et al. |
| 2002/0004196 A1 | 1/2002 | Whitson |
| 2002/0052618 A1 | 5/2002 | Haar et al. |
| 2002/0076349 A1 * | 6/2002 | Aitken et al. |
| 2002/0076357 A1 * | 6/2002 | Hahs et al. |
| 2002/0082543 A1 | 6/2002 | Park et al. |
| 2002/0103499 A1 | 8/2002 | Perez et al. |
| 2002/0188224 A1 * | 12/2002 | Roe et al. |
| 2003/0083685 A1 * | 5/2003 | Freeman et al. |
| 2003/0088191 A1 | 5/2003 | Freeman et al. |
| 2003/0191415 A1 * | 10/2003 | Moerman et al. ........... 600/584 |
| 2003/0211619 A1 | 11/2003 | Olson et al. |
| 2003/0233112 A1 | 12/2003 | Alden et al. |
| 2003/0233113 A1 | 12/2003 | Alden et al. |
| 2004/0138688 A1 * | 7/2004 | Giraud |
| 2004/0249311 A1 | 12/2004 | Haar et al. |

FOREIGN PATENT DOCUMENTS

| | | |
|---|---|---|
| DE | 198 57 426 A1 | 6/2000 |
| DE | 101 05 549 A1 | 8/2002 |
| EP | 0 299 517 B1 | 6/1993 |
| EP | 0 351 891 B1 | 9/1993 |
| EP | 0 637 749 A2 * | 2/1995 |
| EP | 1 203 563 A2 * | 5/2002 |
| EP | 1 321 769 A1 * | 6/2003 |
| EP | 1 424 040 A1 | 6/2004 |
| JP | 1105157 A1 * | 4/1989 |
| JP | 04194660 A1 | 11/1990 |
| JP | 05-010951 * | 1/1993 |
| JP | 5045363 A1 * | 2/1993 |
| JP | 9-276235 | 10/1997 |
| JP | 2000116768 A2 | 4/2000 |
| WO | WO 93/02720 A1 | 2/1993 |
| WO | WO 93/09710 A1 * | 5/1993 |
| WO | WO 93/12726 | 7/1993 |
| WO | WO 97/42888 | 11/1997 |
| WO | WO 01/00090 A1 | 1/2001 |
| WO | WO 01/08551 A2 | 2/2001 |
| WO | WO 01/34029 A1 | 5/2001 |
| WO | WO 01/66010 A1 | 9/2001 |
| WO | WO 02/18940 A2 * | 3/2002 |
| WO | WO 02/056769 A1 | 7/2002 |
| WO | WO 2004/047642 A2 | 6/2004 |
| WO | WO 2004/060174 A2 * | 7/2004 |

* cited by examiner

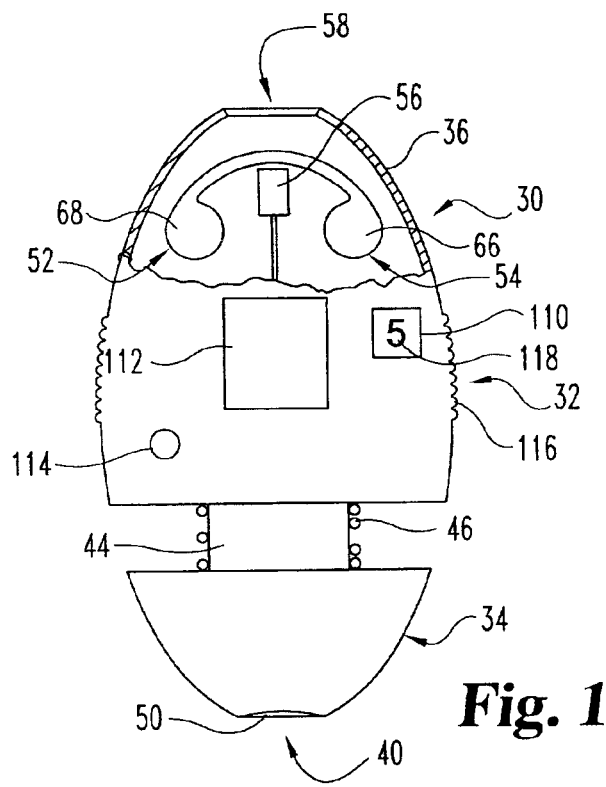
*Fig. 1*
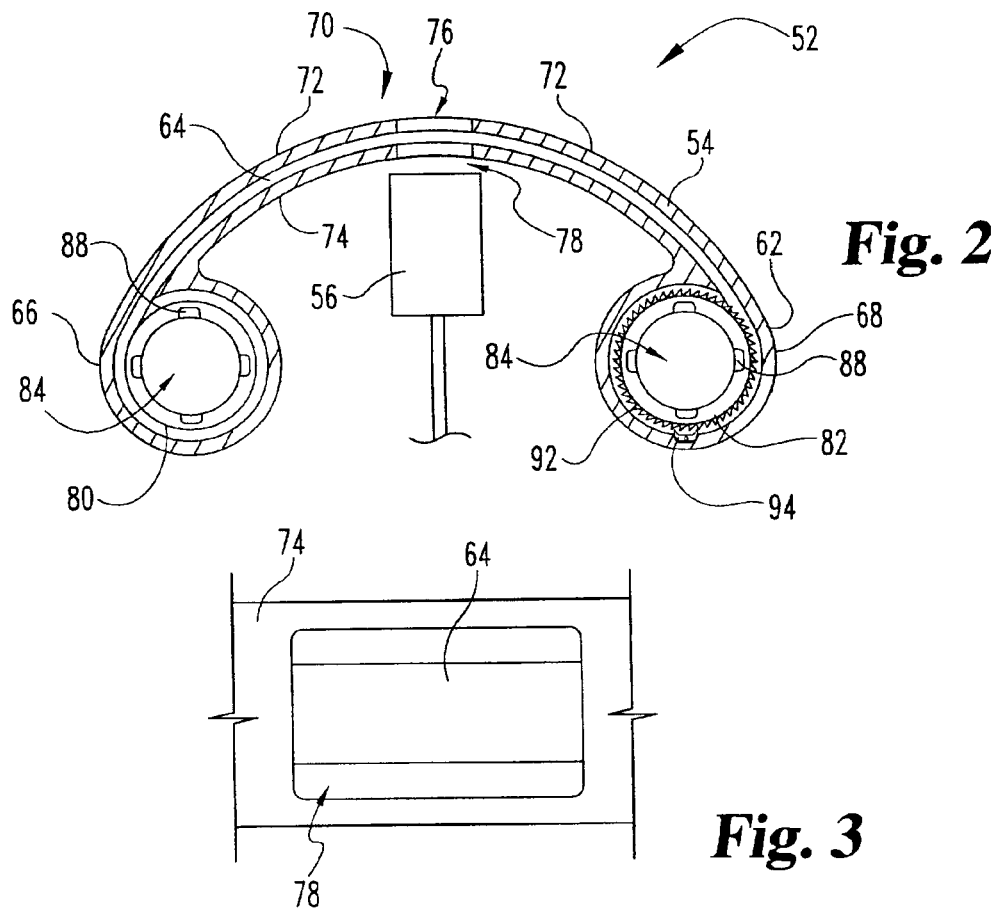
*Fig. 2*
*Fig. 3*

TEST MEDIA CASSETTE FOR BODILY FLUID TESTING DEVICE

REFERENCE TO RELATED APPLICATIONS

This application claims the benefit of U.S. Provisional Patent Application No. 60/296,989, filed Jun. 8, 2001, which is hereby incorporated by reference in its entirety.

BACKGROUND OF THE INVENTION

The present invention relates to bodily fluid sampling devices, and more specifically, but not exclusively, concerns a bodily fluid sampling device that incorporates a test media cassette that contains test media used to test bodily fluid.

General Fluid Testing

The acquisition and testing of bodily fluids is useful for many purposes, and continues to grow in importance for use in medical diagnosis and treatment, and in other diverse applications. In the medical field, it is desirable for lay operators to perform tests routinely, quickly and reproducibly outside of a laboratory setting, with rapid results and a readout of the resulting test information. Testing can be performed on various bodily fluids, and for certain applications is particularly related to the testing of blood and/or interstitial fluid. Such fluids can be tested for a variety of characteristics of the fluid, or analytes contained in the fluid, in order to identify a medical condition, determine therapeutic responses, assess the progress of treatment, and the like.

General Test Steps

The testing of bodily fluids basically involves the steps of obtaining the fluid sample, transferring the sample to a test device, conducting a test on the fluid sample, and displaying the results. These steps are generally performed by a plurality of separate instruments or devices.

Acquiring—Vascular

One method of acquiring the fluid sample involves inserting a hollow needle or syringe into a vein or artery in order to withdraw a blood sample. However, such direct vascular blood sampling can have several limitations, including pain, infection, and hematoma and other bleeding complications. In addition, direct vascular blood sampling is not suitable for repeating on a routine basis, can be extremely difficult and is not advised for patients to perform on themselves.

Acquiring—Incising

The other common technique for collecting a bodily fluid sample is to form an incision in the skin to bring the fluid to the skin surface. A lancet, knife or other cutting instrument is used to form the incision in the skin. The resulting blood or interstitial fluid specimen is then collected in a small tube or other container, or is placed directly in contact with a test strip. The fingertip is frequently used as the fluid source because it is highly vascularized and therefore produces a good quantity of blood. However, the fingertip also has a large concentration of nerve endings, and lancing the fingertip can therefore be painful. Alternate sampling sites, such as the palm of the hand, forearm, earlobe and the like, may be useful for sampling, and are less painful. However, they also produce lesser amounts of blood. These alternate sites therefore are generally appropriate for use only for test systems requiring relatively small amounts of fluid, or if steps are taken to facilitate the expression of the bodily fluid from the incision site.

Various methods and systems for incising the skin are known in the art. Exemplary lancing devices are shown, for example, in U.S. Pat. No. Re 35,803, issued to Lange, et al. on May 19, 1998; U.S. Pat. No. 4,924,879, issued to O'Brien on May 15, 1990; U.S. Pat. No. 5,879,311, issued to Duchon et al. on Feb. 16, 1999; U.S. Pat. No. 5,857,983, issued to Douglas on Jan. 12, 1999; U.S. Pat. No. 6,183,489, issued to Douglas et al. on Feb. 6, 2001; U.S. Pat. No. 6,332,871, issued to Douglas et al. on Dec. 25, 2001; and U.S. Pat. No. 5,964,718, issued to Duchon et al. on Oct. 12, 1999. A representative commercial lancing device is the Accu-Chek Softclix lancet.

Expressing

Patients are frequently advised to urge fluid to the incision site, such as by applying pressure to the area surrounding the incision to milk or pump the fluid from the incision. Mechanical devices are also known to facilitate the expression of bodily fluid from an incision. Such devices are shown, for example, in U.S. Pat. No. 5,879,311, issued to Duchon et al. on Feb. 16, 1999; U.S. Pat. No. 5,857,983, issued to Douglas on Jan. 12, 1999; U.S. Pat. No. 6,183,489, issued to Douglas et al. on Feb. 6, 2001; U.S. Pat. No. 5,951,492, issued to Douglas et al. on Sep. 14, 1999; U.S. Pat. No. 5,951,493, issued to Douglas et al. on Sep. 14, 1999; U.S. Pat. No. 5,964,718, issued to Duchon et al. on Oct. 12, 1999; and U.S. Pat. No. 6,086,545, issued to Roe et al. on Jul. 11, 2000. A representative commercial product that promotes the expression of bodily fluid from an incision is the Amira AtLast blood glucose system.

Sampling

The acquisition of the produced bodily fluid, hereafter referred to as the "sampling" of the fluid, can take various forms. Once the fluid specimen comes to the skin surface at the incision, a sampling device is placed into contact with the fluid. Such devices may include, for example, systems in which a tube or test strip is either located adjacent the incision site prior to forming the incision, or is moved to the incision site shortly after the incision has been formed. A sampling tube may acquire the fluid by suction or by capillary action. Such sampling systems may include, for example, the systems shown in U.S. Pat. No. 6,048,352, issued to Douglas et al. on Apr. 11, 2000; U.S. Pat. No. 6,099,484, issued to Douglas et al. on Aug. 8, 2000; and U.S. Pat. No. 6,332,871, issued to Douglas et al. on Dec. 25, 2001. Examples of commercial sampling devices include the Roche Compact, Amira AtLast, Glucometer Elite and Therasense FreeStyle test strips.

Testing General

The bodily fluid sample may be analyzed for a variety of properties or components, as is well known in the art. For example, such analysis may be directed to hematocrit, blood glucose, coagulation, lead, iron, etc. Testing systems include such means as optical (e.g., reflectance, absorption, fluorescence, Raman, etc.), electrochemical, and magnetic means for analyzing the sampled fluid. Examples of such test systems include those in U.S. Pat. No. 5,824,491, issued to Priest et al. on Oct. 20, 1998; U.S. Pat. No. 5,962,215, issued to Douglas et al. on Oct. 5, 1999; and U.S. Pat. No. 5,776,719, issued to Douglas et al. on Jul. 7, 1998.

Typically, a test system takes advantage of a reaction between the bodily fluid to be tested and a reagent present in the test system. For example, an optical test strip will generally rely upon a color change, i.e., a change in the wavelength absorbed or reflected by dye formed by the reagent system used. See, e.g., U.S. Pat. Nos. 3,802,842; 4,061,468; and 4,490,465.

Blood Glucose

A common medical test is the measurement of blood glucose level. The glucose level can be determined directly by analysis of the blood, or indirectly by analysis of other fluids such as interstitial fluid. Diabetics are generally instructed to measure their blood glucose level several times a day, depending on the nature and severity of their diabetes. Based upon the observed pattern in the measured glucose levels, the patient and physician determine the appropriate level of insulin to be administered, also taking into account such issues as diet, exercise and other factors.

In testing for the presence of an analyte such as glucose in a bodily fluid, test systems are commonly used which take advantage of an oxidation/reduction reaction which occurs using an oxidase/peroxidase detection chemistry. The test reagent is exposed to a sample of the bodily fluid for a suitable period of time, and there is a color change if the analyte (glucose) is present. Typically, the intensity of this change is proportional to the concentration of analyte in the sample. The color of the reagent is then compared to a known standard which enables one to determine the amount of analyte present in the sample. This determination can be made, for example, by a visual check or by an instrument, such as a reflectance spectrophotometer at a selected wavelength, or a blood glucose meter. Electrochemical and other systems are also well known for testing bodily fluids for properties on constituents.

Testing Media

As mentioned above, diabetics typically have to monitor their blood glucose levels throughout the day so as to ensure that their blood glucose remains within an acceptable range. Some types sampling devices require the use of testing strips that contain media for absorbing and/or testing the bodily fluid, such as blood. After testing, the testing media contaminated with blood can be considered a biohazard and needs to be readily disposed in order to avoid other individuals from being exposed to the contaminated test strip. This can be especially inconvenient when the person is away from home, such as at restaurant. Moreover, the individual test strips can become easily mixed with other test strips having different expiration dates. The use of expired test strips may create false readings, which can result in improper treatment of the patient, such as improper insulin dosages for diabetics.

SUMMARY OF THE INVENTION

The present invention provides various systems and methods for sampling bodily fluid. The present invention encompasses a bodily fluid sampling device that incorporates a cassette containing test media.

In accordance with one aspect of the present invention, there is provided a bodily fluid sampling device for analyzing a bodily fluid. The sampling device includes a test media cassette that includes a test media tape adapted to collect the bodily fluid. The cassette includes a supply portion that stores an uncontaminated section of the test media tape, which is uncontaminated with the bodily fluid. A storage portion stores a contaminated section of the test media tape that is contaminated with the bodily fluid. An exposure portion is positioned between the supply portion and the storage portion. The exposure portion is adapted to expose a section of the test media tape to the bodily fluid. A sensor is positioned between the supply portion and the storage portion to sense at least one property of the bodily fluid collected on the test media tape at the exposure portion of the cassette.

Another aspect of the present invention concerns a test cassette for collecting a bodily fluid sample. The cassette includes a test media tape, which has a contaminated section that is contaminated with past samples of the bodily fluid and an uncontaminated section. The cassette includes a housing that has a supply portion in which the uncontaminated section of the test media tape is enclosed. The housing further includes a storage portion in which the contaminated section of the test media tape is enclosed. The housing defines an exposure opening along the test media tape at which the test media tape is exposed to the bodily fluid. A supply reel is disposed in the supply portion of the housing around which the uncontaminated section of the test media tape is wrapped. A storage reel is disposed in the storage portion of the housing around which the contaminated section of the test media tape is wrapped.

Other forms, embodiments, objects, features, advantages, benefits and aspects of the present invention shall become apparent from the detailed drawings and description contained herein.

BRIEF DESCRIPTION OF THE DRAWINGS

FIG. 1 is a partial, cross-sectional view of a bodily fluid sampling device according to one embodiment of the present invention.

FIG. 2 is a cross-sectional view of a test cassette and sensor used in the FIG. 1 sampling device.

FIG. 3 is a partial, side view of the FIG. 2 cassette.

DESCRIPTION OF SELECTED EMBODIMENTS

Figure 4:
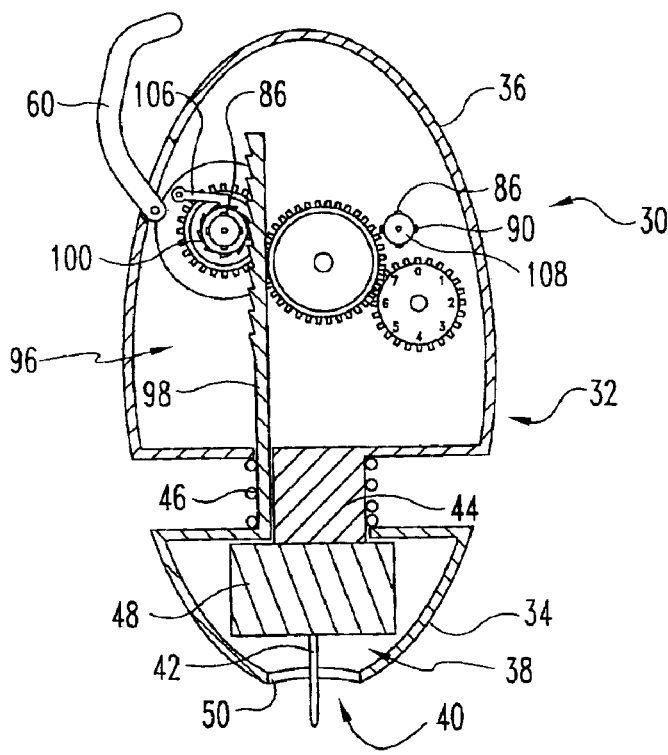
FIG. 4 is a cross-sectional view of the FIG. 1 sampling device.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. One embodiment of the invention is shown in great detail, although it will be apparent to those skilled in the art that some of the features which are not relevant to the invention may not be shown for the sake of clarity.

The present invention concerns a bodily fluid sampling device that incorporates a test cassette. The cassette houses test media that is used to collect bodily fluid samples which are analyzed with a sensor in the sampling device. The test media in the cassette is indexed before or after each test so that successive tests can be performed without requiring disposal of the used test media. The test media can be indexed manually or automatically. In one aspect of the present invention, the test media includes a cover tape that protects the test media before testing. In another aspect, the test media defines one or more passageways through which a piercing device is able to pass through in order to pierce the skin of a user. The cassette, in another aspect of the present invention, is designed for use with a vacuum-style sampling device in which the bodily fluid sample is drawn to the test media by a vacuum.

A bodily fluid sampling device 30 according to one embodiment of the present invention is illustrated in FIGS. 1–5. As shown in FIGS. 1 and 4, the sampling device 30 includes a housing 32 with a piercing end portion 34 and an opposite, sampling end portion 36. The piercing portion 34 of the housing 32 is slidable relative to the sampling portion 36. As shown in FIG. 4, piercing portion 34 defines a piercing device cavity 38 with a piercing device opening 40. In the piercing cavity 38, a piercing device or member 42, which is used for puncturing skin, is covered by the piercing portion 34 of the housing 32 to avoid accidental piercing of the skin. The piercing device 42 cuts an incision in the skin such that the bodily fluid, such as blood, pools on the surface of the skin. In one embodiment, the piercing device 42 includes a lancet suitable to puncture the cutaneous layer of the skin. As should be appreciated, other types of piercing devices 42 can also be used, such as needles and blades, to name a few.

As illustrated in FIG. 4, the piercing portion 34 of the housing 32 is slidably received on a slide member 44 that extends from the sampling portion 36 of the housing 32. The piercing device 42 is removably coupled to the slide member 44. A spring 46 on the slide member 44 biases the piercing portion 34 of the housing 32 away from the sampling portion 36, and a stop member 48 on the slide member 44 prevents the piercing portion 34 from sliding off the slide member 44. Normally, the piercing portion 34 of the housing 32 covers the piercing device 42. Once the piercing portion 34 is pressed against the skin, the piercing portion 34 retracts towards the sampling portion 36 of the housing 32 to expose the piercing device 42 through opening 40. In the illustrated embodiment, the piercing portion 34 of the housing 32 has a compression ring 50 around opening 40 in order to draw the bodily fluid to the surface of the skin. In one form, the compression ring 50 is clear so that the user can view the pooling of the bodily fluid.

Referring to FIG. 1, the bodily fluid sampling device 30 includes a sampling system 52 for sampling and testing the drawn bodily fluid. As shown, the sampling system 52 includes a test cassette 54 and a sensor 56. In one embodiment, the sensor 56 is an optical sensor that includes a light source and a detector for determining the amount of light reflected from the collected sample. It should be appreciated, however, that other types of sensors 56 can be used to monitor analyte levels in bodily fluid. For example, the sensor 56 can include an electrical type sensor that measures the electrical and/or electrochemical properties of the sample. The sampling portion 36 of the housing 32 defines a bodily fluid acquisition opening 58 through which the bodily fluid is supplied to the cassette 54. In one embodiment, the cassette 54 is removably coupled to the sampling device 30 such that the cassette 54 can be replaced with a new one. A pivotal cover 60 is pivotally mounted to the housing 32. The cover 60 can be opened to allow disposal and replacement of the cassette 54.

As shown in greater detail in FIGS. 2 and 3, the cassette 54 has an outer casing 62 that encloses test media 64. In the illustrated embodiment, the test media 64 is in the form of a continuous strip or tape. As will be appreciated, the test media 64 can be further segmented into discrete test sections. The casing 62 of the cassette 54 defines an unexposed test media supply portion 66, which stores unused test media 64, and an exposed test media storage portion 68, which stores used test media 64. Connecting together the unexposed 66 and exposed 68 media portions, an exposure/testing portion 70 is configured to allow the bodily fluid to be collected and tested on the test media 64. As shown, the testing portion 70 has outboard sidewall 72 and an opposite, inboard sidewall 74. On the outboard sidewall 72 of the cassette 54, the casing 62 defines an exposure opening 76 at which the test media 64 is exposed to the bodily fluid. Opposite the exposure opening 76, the inboard sidewall 74 of the casing 62 defines a test opening 78 at which the sensor 56 is able to analyze the bodily fluid collected on the test media 64. In the illustrated embodiment, the exposure 76 and test 78 openings are aligned with another. In other embodiments, openings 76 and 78 can be instead offset from one another. For instance, the testing opening 78 can be located closer towards the exposed media storage portion 68, as compared to exposure opening 76.

In the unexposed media storage portion 66 of the cassette 54, a supply reel 80 is rotatably mounted, and unused test media 64 is wrapped around the supply reel 80. Similarly, the exposed media storage portion 68 has a take-up reel 82 rotatably mounted inside. Test media 64 that has been exposed to the bodily fluid at the exposure opening 76 is wrapped around the take-up reel 82. It should be appreciated that in other embodiments, one or both of the reels 80, 82 can be omitted from the cassette 54. Both reels 80 and 82 define drive cavities 84 that can be engaged with drive members 86 in the sampling end portion 36 of the sampling device 30 (FIG. 4). As shown in FIGS. 2 and 4, the drive cavities 84 have notches 88 that mate with flanges 90 on the drive members 86 such that the drive members 86 are able to rotate the reels 80 and 82. To ensure that the used test media 54 is not removed from the exposed media storage portion 68 of the cassette 54, the take-up reel 82 has a geared portion 92 that engages a biased, cassette pawl 94 that permits the take-up reel 82 to rotate in only one direction. This ensures that the test media 64 can only be fed into exposed media storage portion 68 and not removed.

Figure 5:
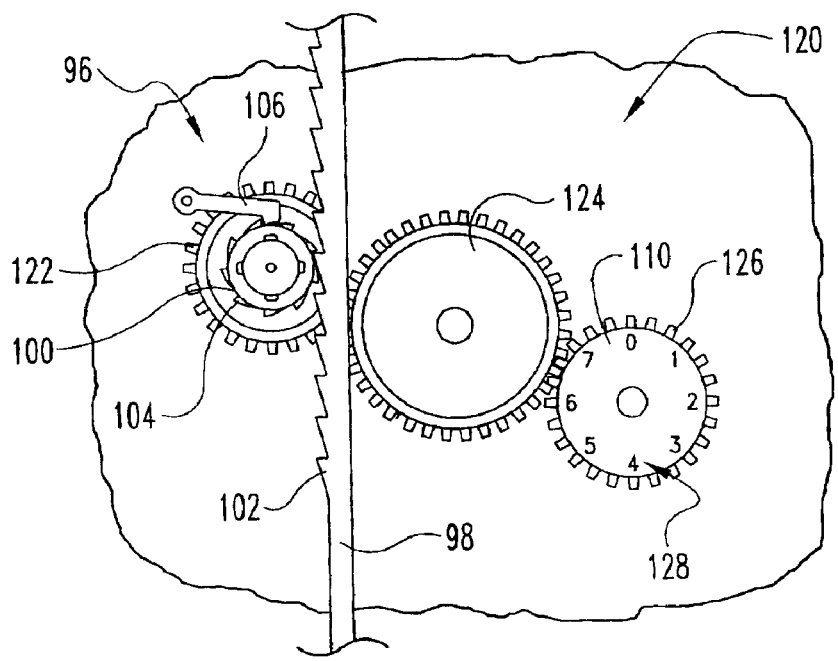
FIG. 5 is a front view of an indexing mechanism used in the FIG. 1 sampling device.

As shown in FIGS. 4 and 5, the sampling device 30 further incorporates an advancement or indexing device 96 that advances the test media 64 in the cassette 54 such that fresh test media 54 is available every time a bodily fluid sample is taken. In the illustrated embodiment, a mechanical type advancement device 96 is used to advance the test media 64. However, it should be appreciated that an electrical or a combination electro-mechanical type advancement device 96 may also be used. In FIG. 4, the advancement device 96 includes a rack member 98 that is attached to the piercing portion 34 of the housing 32. The rack member 98 extends from the piercing portion 34 and terminates proximal to take-up drive member 100. The take-up drive member 100 is constructed to engage and rotate the take-up reel 82 in the cassette 54. The rack member 98 has rack teeth 102 that engage take-up drive teeth 104 on the take-up drive member 100. To ensure that the take-up drive member 100 only rotates in one direction, the advancement device 96 has an advancement pawl 106 attached to the housing 32 and biased against the take-up drive teeth 104. As shown in FIG. 5, both teeth 102 and 104 are angled in such a manner to only firmly engage one another when rotating the take-up drive member 100 in a counterclockwise fashion (from the perspective of FIG. 5). In the illustrated embodiment, only the take-up drive member 100 is powered, while supply drive member 108 is able to freely rotate. In other embodiments, both drive members 100 and 108 may be powered individually or together. For instance, when an electro-mechanical type advancement device 96 is used, both drive members 100 and 108 can be individually powered by separate electric motors.

Referring again to FIG. 1, the bodily fluid sampling device 30 further includes a test indicator 110, a display 112, at least one control button 114, and a grip portion 116. In the illustrated embodiment, the grip portion 116 has ridges that help ensure the user has a firm grip on the sampling device 30. The test indicator 110 can either indicate the number of tests performed or the number of tests remaining on the current cassette 54. The housing 32 has an indicator window 118 through which the indicator 110 can be viewed. The display 112 is operatively coupled to the sensor 56 and displays readings from the sensor 56. The button 114 is used to control and enter information into the bodily fluid sampling device 30. In the illustrated embodiment, the indicator 110 and the display 112 are separate components. However, it should be appreciated that the indicator 110 can be incorporated into the display 112 to form a single unit.

A detailed view of a test indicator assembly 120, which moves the indicator 110, according to one embodiment of the present invention is illustrated in FIG. 5. As shown, the take-up drive member 100 has a gear 122 that engages an intermediate gear 124. The intermediate gear 124 engages an indicator gear 126 that is attached to the indicator 110. The indicator 110 has numbering 128, or other types of characters, that indicates the number of samples taken with the cassette 54 or the number of tests remaining on the cassette 54. As the take-up drive member 100 is rotated by the rack member 98, the intermediate gear 124 rotates, which in turn rotates the indicator. Although in the illustrated embodiment of the test indicator assembly 120 is mechanically driven, it should be appreciated that the indicator 110 can be operated in other manners, such as electronically.

In operation, the user presses opening 40 of the piercing portion 34 against the skin. The piercing portion 34 of the housing 32 retracts towards the sampling portion 36 exposing the piercing device 42 so as to pierce the skin. As the piercing portion 34 retracts, the rack member 98 rotates the take-up drive 100 in order to advance the test media 64 in the cassette 54 such that unused test media 64 is available for testing. Once the user creates a bodily fluid sample with the piercing device 42, the user places opening 58 over the bodily fluid sample. A portion of the bodily fluid sample travels via direct or capillary action to the unused test media 64 exposed at exposure opening 76 of the cassette 54. When a portion of the bodily fluid sample deposits on the test media 64, the sensor 56 determines the amount of analyte material in the sample. The readings from the sensor 56 are shown on the display 112. During the next test, the cassette 54 is indexed in response to pressing the sampling device 30 against the skin so as to move the contaminated portion of the test media 64 into the storage portion 68 of the cassette 54. As should be appreciated, the sampling device 30 can be instead configured to advance the test media 64 after the bodily fluid sample has been collected or analyzed.

As should be appreciated, the cassette 54 allows a user to perform a number of tests without replacing the test media 64. Once the test media 64 has been completely used, the contaminated test media 64 in the cassette 54 can be safely discarded. In one embodiment, the cassette 54 allows the user to perform a number of tests within a range from about five (5) tests to about five-hundred (500) tests. In another embodiment, the cassette 54 is adapted to perform five (5) to fifty (50) tests before being replaced, and in a further embodiment, the cassette 54 is designed to perform around twenty-five (25) tests. With the above described configuration, the cassette 54 according to the present invention minimizes the amount of biohazard material generated after each test because a test strip does not have to be discarded after each test. Further, since test strips do not have to be individually inserted and removed during each test, the ease of use and convenience is improved with the cassette 54 according to the present invention. Moreover, the cassette 54 obviates the need for the user to carry a vile containing the test strips.

Figure 6:
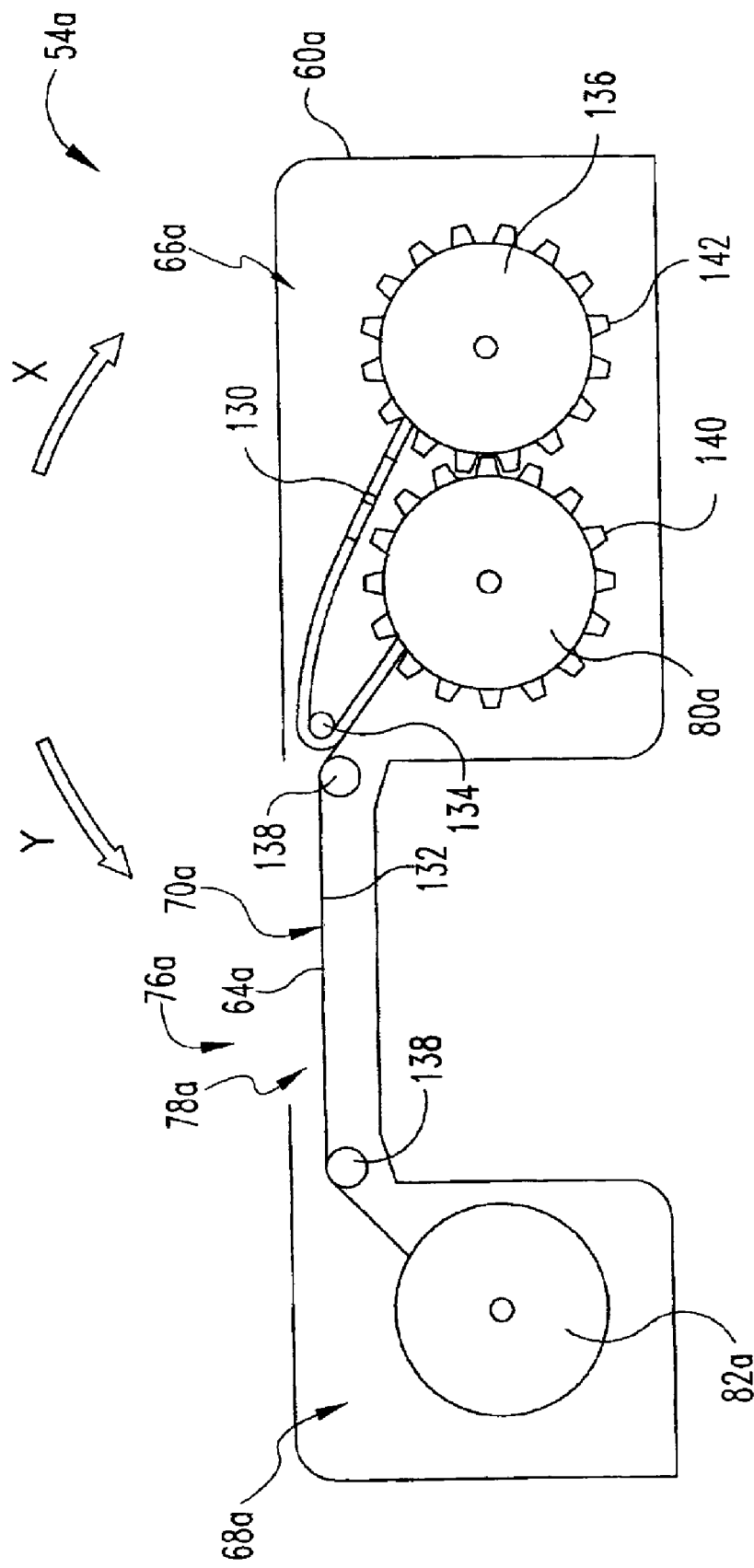
FIG. 6 is a cross-sectional view of a test cassette according to another embodiment of the present invention.

A cassette 54a according to another embodiment of the present invention is illustrated in FIG. 6. As shown, the cassette 54a has an outer cover 60a with an unexposed media supply portion 66a and an exposed media storage portion 68a. The exposed portion 68a of the cover 60a houses a take-up reel 82a, while the unexposed portion 66a houses a supply reel 80a. The test media 64a extends between and is wrapped around both the supply reel 80a and the take-up reel 82a. In the illustrated embodiment, the test media 64a has a cover tape 130 that covers a test tape 132. The cover tape 130 provides an airtight seal over the test tape 132 in order to preserve test chemicals on the test tape 132 while the sampling device 30 is not in use. As illustrated, the cassette 54a further includes a peel tab 134, a cover reel 136 and guides 138 to guide the test media 64a between reels 80a and 82a. The peel tab 134 along with the cover reel 136 are configured to peel the cover tape 130 from the test tape 132. To synchronize rotation of the supply reel 80a and the cover reel 136, the supply reel 80a and the cover reel 136 respectively have a supply gear 140 and a cover gear 142 that are intermeshed with one another. In another embodiment, the rotation of the cover reel 136 is synchronized with the take-up reel 82a.

During use, as the take-up reel 82a is indexed by the sampling device 30, both the supply reel 80a and the cover reel 136 are rotated in unison through gears 140 and 142. As the cover reel 136 rotates, the tension formed on the cover tape 130 between the cover reel 136 and the peel tab 134 causes the cover tape 130 to be pulled from the test tape 132 at the peel tab 134. The peeled cover tape 130 is wrapped around and stored on the cover reel 136. After the cover tape 130 is removed, the test tape 132 is exposed to the bodily fluid sample at an exposure opening 76a formed in the cover 60a. The now exposed test tape 132 can be tested at testing opening 78a that is incorporated into the exposure opening 76a. During the next index of the cassette 54a, the used test tape 132 is wrapped around and stored on the take-up reel 82a.

Figure 7:
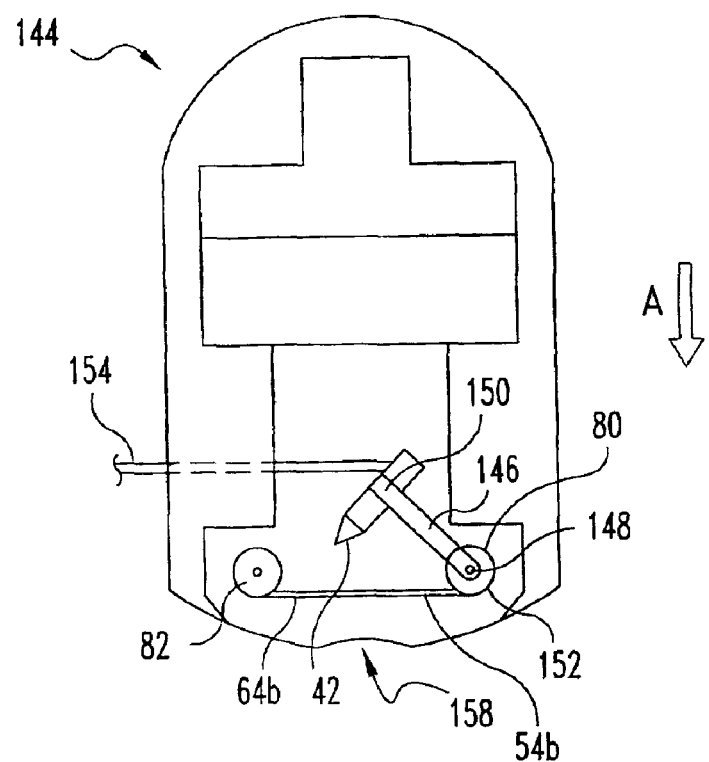
FIG. 7 is a cross-sectional view of a bodily fluid sampling device according to another embodiment of the present invention.

A bodily fluid sampling device 144 according to another embodiment of the present invention is illustrated in FIG. 7. The sampling device 144 includes a cassette 54b and a pivot arm 146 with a pivot end 148 pivotally mounted to the cassette 54b. Opposite the pivot end 148, at free end 150, the pivot arm 146 is coupled to piercing device 42. A spring 152 mounted between the cassette 54b and the pivot arm 146 biases the free end 150 of the pivot arm 146 to move towards the cassette 54b in the direction indicated by arrow A in FIG.

7. A release mechanism 154 is coupled to the free end 150 of the pivot arm 146 in order to bias the piercing device 42 away from the cassette 54b. The cassette 54b includes a supply reel 80, a take-up reel 82 and a test media 64b extending between and wrapped around both reels 80, 82. As illustrated, housing 156 of the sampling device 144 defines a sample opening 158 through which the bodily fluid sample is collected. The test media 64b of the cassette 54 is positioned over the sample opening 158 between the opening 158 and the piercing device 42.

Figure 8:
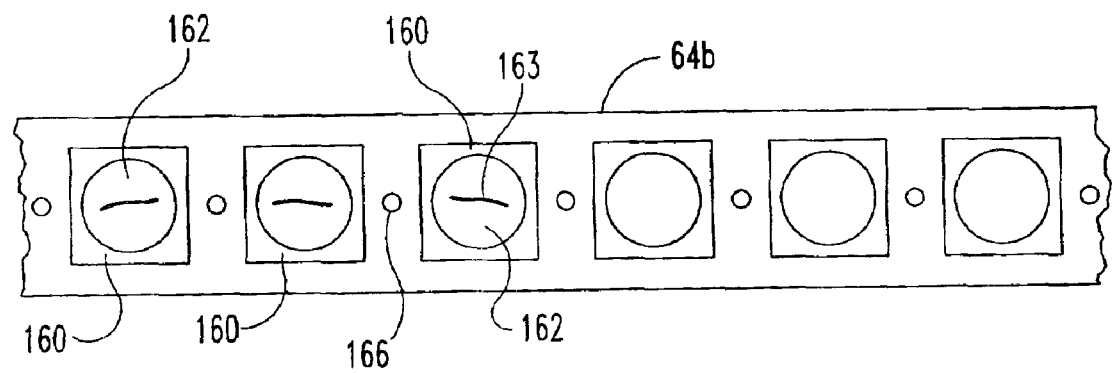
FIG. 8 is a front view of test media used in the FIG. 7 sampling device.
Figure 9:
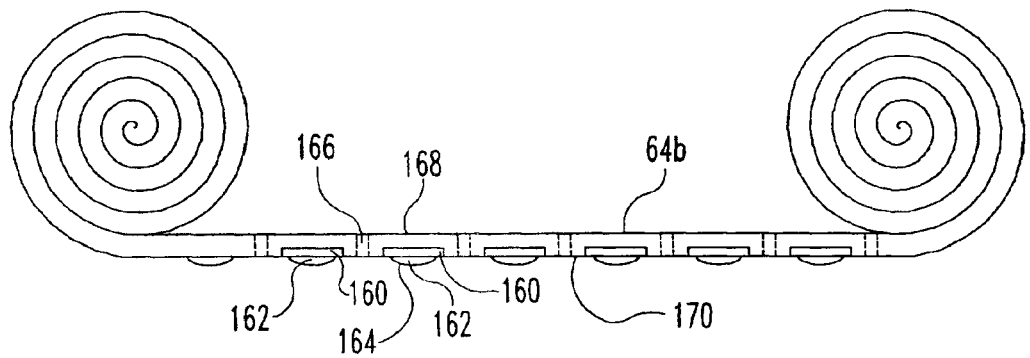
FIG. 9 is a side view of the FIG. 8 test media.
Figure 10:
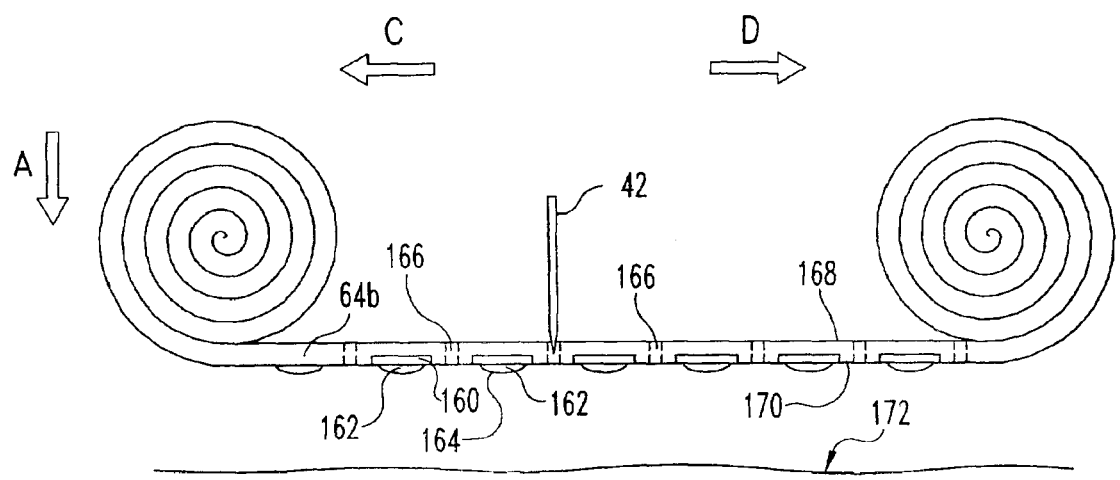
FIG. 10 is a side view of the FIG. 8 test media with a piercing device from the FIG. 7 sampling device.

As shown in further detail in FIGS. 8, 9 and 10, the test media 64b in this embodiment includes a number of test pads 160 spaced apart from one another along the test media 64b. In one embodiment, the test pads 160 contain chemicals reactive to specific constituents contained in the bodily fluid. In one form, the test pad 160 includes a chemistry pad available in an AT LAST™ Blood Glucose System available from Amira Medical located in Scotts Valley, Calif. In another embodiment, the bodily fluid sample is collected on the test pad 160 for electrical and/or optical analysis. Over each test pad 160, the test media 64b has a blister pack 162 that is used to draw the bodily fluid through capillary action onto the test pad 160. During indexing of the test media 64b, a capillary opening 163 (FIG. 8), such as a slit or hole, is cut or pierced into the blister pack 162 by a cutting device, such as razor, in the fluid sampling device 144. In the illustrated embodiment, the opening 163 is in the form of a slit. The capillary slit 163 is used to draw the bodily fluid into the blister pack 162 through capillary action. In the illustrated embodiment the blister pack 162 has a circular shape that fits inside the rectangularly shaped test pad 160 such that portions of the test pad 160 extend past the blister pack 164. In one form, the blister pack 164 is a plastic film covering the test pad 160 and attached to the test media 64b through an adhesive and/or heat sealing. Moreover, in one embodiment, the test media 64b is transparent or semitransparent to allow optical analysis of the bodily fluid. As illustrated in FIGS. 9 and 10 each blister pack 162 has a convex surface 164 that aids in drawing the fluid up to the test pad 160 through the slit 163 via capillary action. To be near the skin in order to collect bodily fluid, both the test pad 160 and the blister pack 162 are positioned on the outboard side 170 of the test media 64b. In another embodiment, the blister pack 162 is omitted such that the bodily fluid directly contacts the test pad 160 during collection of the bodily fluid. Between each test pad 160, the test media 64b defines a piercing device hole or throughway 166. The piercing device throughway 166 extends from inboard side 168 to outboard side 170 of the test media 64b. The throughway 166 is sized such that the piercing device 42 is able to extend through the test media 64b in order to pierce the skin. In another embodiment, the test media 64b is designed to be pierced by the piercing device 42 such that the throughway 166 is not required.

During testing, the user places sample opening 158 of the sampling device 144 against his or her skin 172 (FIGS. 7 and 10). Next, the user disengages the release 154 such that the piercing device 42 on the pivotal arm 146 moves toward the test media 64b. As the pivot arm 146 rotates, the piercing device 42 extends through the throughway 166 and pierces the skin 172 (FIG. 10). After piercing the skin 172, the piercing device 42 retracts away from the skin 172 and out of the throughway 166. In one embodiment, the piercing device 42 is retracted through recoil of a firing spring that is used to initially advance the piercing device 42 to lance the skin 172. At the site where the skin 172 was pierced, the bodily fluid collects and is drawn up by the slit 163 in the blister pack 162 to the test pad 160 via capillary action. To store used test media 64b on the take-up reel 82, the test media 64b in the cassette 54b can be advanced mechanically or manually before or after a test is performed. In one embodiment, the test media 64b in the cassette automatically advances when the pivot arm 146 swings toward the cassette 54b. In another embodiment, the test media 64b is advanced manually after the sample has been collected and tested.

Figure 11:
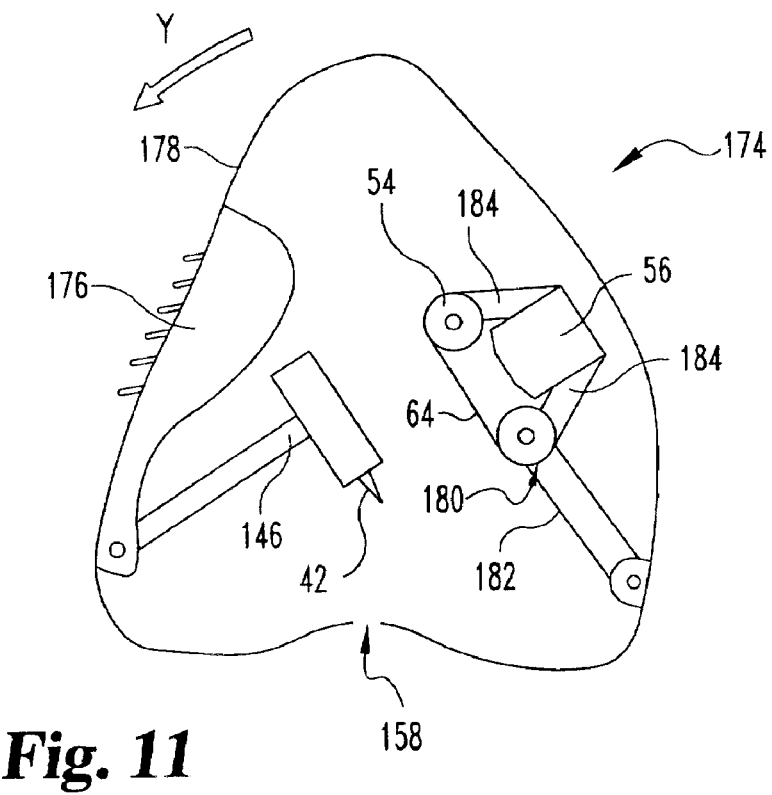
FIG. 11 is a cross-sectional view of a bodily fluid sampling device according to another embodiment of the present invention.

A bodily fluid sampling device 174 according to another embodiment of the present invention is illustrated in FIG. 11. The sampling device 174 has a piercing device 42 coupled to a pivot arm 146 that is pivotally coupled to a trigger mechanism 176. Both the pivot arm 146 and the trigger mechanism 176 of the sampling device 174 are pivotally coupled to a housing 178. The housing 178 defines a sample opening 158. The pivot arm 146 and the piercing device 42 are positioned within the housing 178 such that the piercing device 42 is able to swing through the opening 158 and pierce the skin. The sampling device 174 further includes a cassette-sensor assembly 180 pivotally mounted to the housing 178 through a swing arm 182. As shown, the cassette-sensor assembly 180 includes a cassette 54 and a sensor 56. The sensor 56 is mounted proximal to and in a fixed relationship with the cassette 54 through mounting arms 184. The swing arm 182 of the cassette-sensor assembly 180 can be moved by a number ways. In one embodiment, the swing arm 182 is actuated through a mechanical linkage with the trigger mechanism 176, and in another embodiment, the swing arm 182 is moved by an electric motor.

To take and test a bodily fluid sample, the user presses the sample opening 158 against the skin of the user. The user then cocks the trigger mechanism 176 and releases the trigger mechanism 176 in order to swing the piercing device 42 through the sample opening 158 to pierce the skin of the user. Afterwards, the piercing device 42 retracts back into the housing 178 as a sample of the bodily fluid, such as blood, collects on the skin. In one form, the piercing device 42 is retracted by the recoil of a firing spring that is initially used to lance the skin. To collect and test the bodily fluid sample, the swing arm 182 swings the cassette sensor assembly 180 over the opening 158. After the sample is deposited on the test media 64 in the cassette 54, the sensor 56 analyzes the collected sample. In one form, the sensor 56 is an optical type sensor that analyzes the optical properties of the sample. In another form, the sensor 56 analyzes the electrical properties of the sample.

Figure 12:
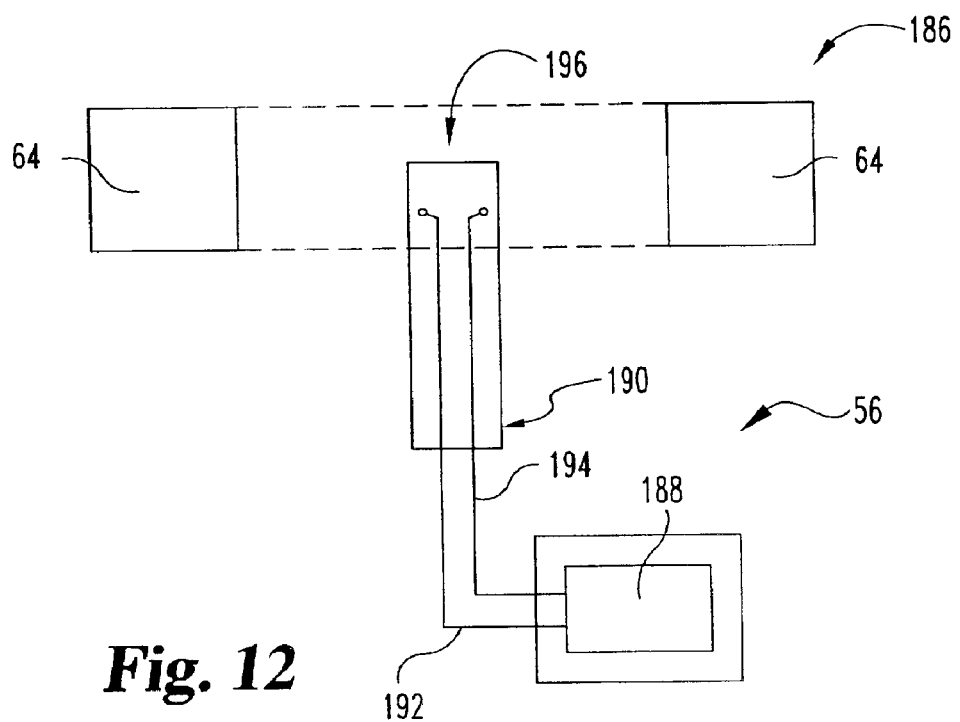
FIG. 12 is a diagrammatic view of a sensor system according to another embodiment of the present invention.

As mentioned above, the sensor 56 can analyze the bodily fluid sample by using a number of techniques. In one embodiment, the sensor 56 analyzes the electrochemical properties of the sample. In another embodiment that is illustrated in FIG. 12, the sensor 56 includes an optical sensor system 186 that remotely detects the optical properties of the sampled bodily fluid. The optical sensor system 186 includes a remotely located light source/detector 188, which can be located inside or outside of the bodily fluid sampling device. The light source/detector 188 employs components suitable for emitting light and for determining the amount and/or frequency of reflected light. By way of nonlimiting example, the light source/detector 188 can include a light emitting diode (LED), a photodiode and the like. With such a construction, the optical sensor system 186 according to the present invention allows for more compact sampling device and cassette designs. As shown, a pair of fiber optic cables 190 are coupled to the light source/detector 188. The fiber optic cables 190 include a transmission cable 192 and a detection cable 194. The fiber optic cables 190 extend from the light source/detector 188 to a test area 196 that is proximal the test media 64. In the test area 196, the transmission cable 192 is coupled to an emitter 198 that is adapted to emit light, and the detection cable 194 is coupled to a detector 200 that is adapted to receive light.

During testing, after the bodily fluid sample has been placed on the test media 64, the light source/detector 188 emits light from the emitter 198 via transmission cable 192. The light emitted from the emitter 198 is reflected off the bodily fluid sample on the test media 64, and the reflected light is detected by the light source/detector 188 via the detector 200. The light/source detector 188 analyzes the amount and/or frequency of the light reflected from the bodily fluid sample in order to determine the amount of analyte in the sample. As used herein and in conventional fashion, reference to analysis of the bodily fluid also includes analysis of the results of a reaction of a selected reagent with the bodily fluid.

Figure 13:
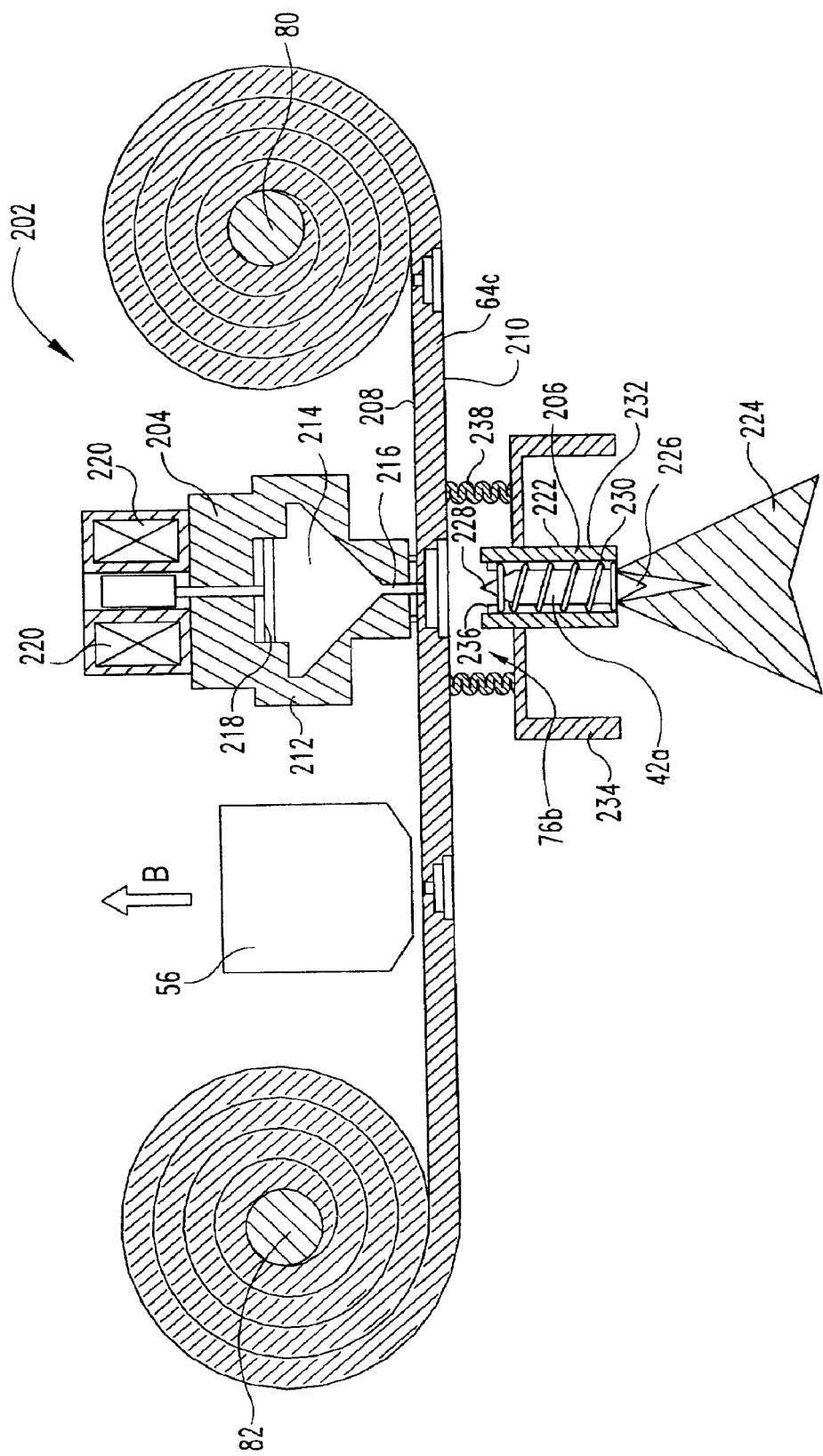
FIG. 13 is a cross-sectional view of a bodily fluid testing system according to another embodiment of the present invention.

A bodily fluid testing system 202 that can be integrated into a sampling device according to the present invention is illustrated in FIG. 13. The testing system 202 includes a vacuum assembly 204, a piercing assembly 206, a sensor 56, and test media 64c. In the illustrated embodiment, the test media 64c is not housed in a cassette case. Rather, the test media 64c is wrapped around and extends between supply reel 80 and take-up reel 82. It should be appreciated that the test media 64c can be encased in a cassette case. As shown, the test media 64c has an inboard side 208 and an opposite, outboard side 210. The vacuum assembly 204, the piercing assembly 206 and the sensor 56 are positioned along the test media 64c between the supply reel 80 and the take-up reel 82. In particular, both the vacuum assembly 204 and the sensor 56 are positioned on the inboard side 208, with the sensor 56 positioned between the take-up reel 82 and the vacuum assembly 204. The piercing assembly 206 is disposed opposite the vacuum assembly 204 on the outboard side 210 of the test media 64c.

The vacuum assembly 204 is adapted to generate a vacuum in order to draw a bodily fluid sample onto and/or into the test media 64c. The vacuum assembly 204 can include, but is not limited to, a pre-charge vacuum device, an electromagnetic diaphragm vacuum device and/or a mechanical vacuum device, to name a few. In the illustrated embodiment, the vacuum assembly 204 has a body 212 that defines a vacuum cavity 214. Near the test media 64c, the body 212 defines a vacuum port 216 that opens into the vacuum cavity 214. A piston 218 is slidably received in the vacuum cavity 214. Solenoids 220 are used to actuate the piston 218 in order to form a vacuum in the vacuum cavity 214.

Figure 15:
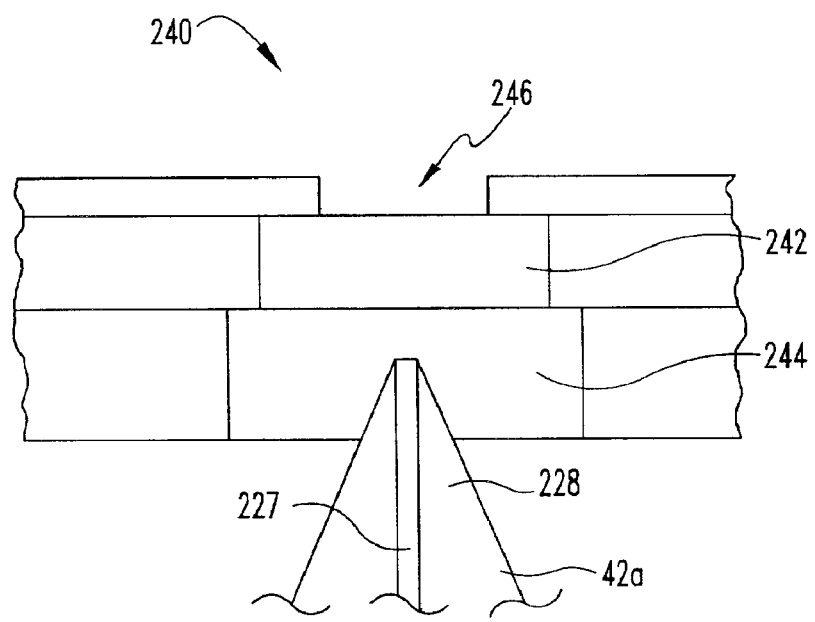
FIG. 15 is an enlarged, cross-sectional view of a portion of the FIG. 14 test media.

As shown in FIG. 13, the piercing assembly 206 includes a piercing device 42a, a holder 222, which holds the piercing device 42a, and a protective cover 224. In the illustrated embodiment, the piercing device 42a has a distal tip 226 adapted to pierce the skin of the user and a proximal tip 228. As depicted in FIG. 15, the piercing device 42a defines a cavity 227 that extends from the distal tip 226 to the proximal tip 228. The cavity 227 transports bodily fluid from the user to the test media 64c. Referring again to FIG. 13, the protective cover 224 covers the distal tip 226 of the piercing device 42a so as to prevent a person from being accidentally cut with the piercing device 42a. The holder 222 includes a coil spring 230 wrapped around the piercing device 42a such that the piercing device 42a is able to be removed and replaced with another piercing device 42a. As shown, the holder 222 has a hollow, inner holder member 232 that is surrounded by an outer holder member 234. The piercing device 42a along with the coil spring 230 are received inside the inner holder member 232. To prevent over-penetration of the proximal tip 228 of the piercing device 42a into the test media 64c during testing, the inner holder member 232 has a stop ridge 236 that engages the piercing device 42a. The holder 222 further includes a collapsible, biasing member 238 that normally biases the piercing device 42a away from the test media 64c. When the holder 222 is pressed against the skin during piercing, the biasing member 238 collapses such that the proximal tip 228 of the piercing device 42a is able to pierce the test media 64c.

Figure 14:
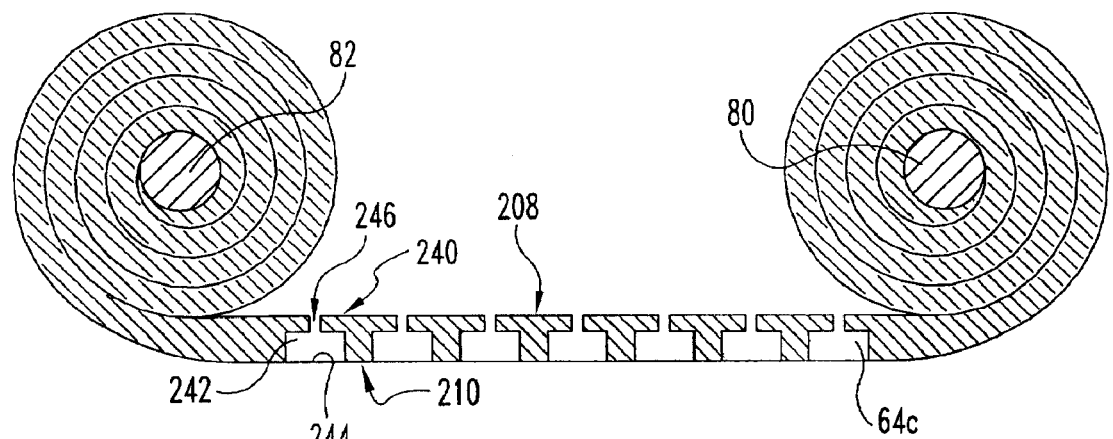
FIG. 14 is a cross-sectional view of test media used in the FIG. 13 sampling device.

As illustrated in FIGS. 14 and 15, the test media 64c has a number of testing sections 240 that are adapted to collect separate bodily fluid samples. Each testing section 240 has a test pad 242 positioned between a seal membrane 244 and a vacuum passageway 246 that is defined in the test media 64c. In one embodiment, the test pad 242 is embedded with chemicals that are reactive with specific bodily fluid constituents for testing purposes. In another embodiment, the test pad 242 is adapted to collect and absorb the bodily fluid sample for analysis by the sensor 56. On the outboard side 210 of the test media 64c, the seal membrane 244 seals over the test membrane 242. On the inboard side 208, the vacuum passageway 246 is adapted to align with the vacuum port 216 of the vacuum assembly 204 such that the vacuum assembly 204 is able to form a vacuum (an area of low pressure) in the vacuum passageway 246 and around the test pad 242. The seal 244 is made of suitable material that allows the vacuum to be maintained around the test pad 242, while at the same time being able to be punctured by the piercing device 42a (FIG. 15). The seal 244 may be formed from various types of sealing materials, such as rubber and/or silicone, to name a few.

As mentioned above, to test a bodily fluid sample, the user presses the holder 222 against the skin in order to pierce the skin with the piercing device 42a. As piercing device 42a pierces the skin, the biasing member 238 collapses to allow the proximal tip 228 to puncture the test media 64c. As shown in FIG. 15, the seal 244 is punctured by and seals around the proximal tip 228. The vacuum assembly 204 forms a vacuum in the vacuum passageway in order to draw the bodily fluid sample onto the test pad 242. Once the sample is collected on the test pad 242, the holder 22 is removed from the skin and the vacuum assembly 204 ceases operation. The test pad 242 is then indexed proximal to the sensor 56 for analysis.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A bodily fluid sampling device for analyzing a bodily fluid, comprising:
   a test media cassette including
   a test media tape adapted to collect the bodily fluid,
   a supply portion storing an uncontaminated section of the test media tape that is uncontaminated with the bodily fluid,
   a storage portion storing a contaminated section of the test media tape that is contaminated with the bodily fluid,
   an exposure portion positioned between the supply portion and the storage portion, the exposure portion being adapted to expose a section of the test media tape to the bodily fluid;

a sensor positioned between the supply portion and the storage portion to sense at least one property of the bodily fluid collected on the test media tape at the exposure portion of the cassette;

a piercing device adapted to pierce skin; and the test media tape defining a throughway to allow passage of the piercing device through the test media tape during piercing.

2. The bodily fluid sampling device of claim 1, wherein:

the supply portion includes a supply reel, wherein the uncontaminated section of the test media tape is wound on the supply reel; and the storage portion includes a storage reel, wherein the contaminated section of the test media tape is wound on the storage reel.

3. The bodily fluid sampling device of claim 2, further comprising:

wherein the test media tape includes a cover tape to preserve the test media tape; and a cover reel attached to the cover tape, the cover reel being adapted to peel the cover tape from the test media tape before exposure to the bodily fluid.

4. The bodily fluid sampling device of claim 1, wherein the test media tape includes:

a test pad containing chemicals for testing the bodily fluid; and a blister pack positioned proximal to the test pad, the blister pack having a raised surface adapted to draw the bodily fluid to the test pad through capillary action.

5. The bodily fluid sampling device of claim 1, further comprising:

a vacuum assembly to generate a vacuum;

a piercing device adapted to pierce skin and draw the bodily fluid;

wherein the test media tape includes separate test sections, each test section including a vacuum passageway defined in the test media and a seal membrane, the seal membrane being adapted to be pierced and seal around the piercing device when the bodily fluid is collected, each test section further including a test pad positioned between the vacuum passageway and the seal membrane, the test pad being adapted to collect the bodily fluid; and wherein the vacuum assembly being adapted to form a vacuum in the vacuum cavity to draw the bodily fluid up the piercing device and onto the test pad during testing.

6. The bodily fluid sampling device of claim 1, further comprising:

a piercing device mounted on a first pivotal arm to pierce skin; and wherein the cassette is coupled to a second pivotal arm to pivot the cassette into position to collect the bodily fluid after the piercing device pierces the skin.

7. The bodily fluid sampling device of claim 1, further comprising:

a piercing device to pierce skin; and an advancement mechanism to advance the test media tape in response to piercing of the skin by the piercing device.

8. The bodily fluid sampling device of claim 7, wherein:

the storage portion includes a storage reel and the contaminated section of the test media tape is wound on the storage reel; and the advancement mechanism includes a movable cover surrounding the piercing device, the movable cover being adapted to move and expose the piercing device during sampling, and a rack member coupled between the movable cover and the storage reel to rotate the storage real upon movement of the movable cover.

9. The bodily fluid sampling device of claim 1, further comprising an indicator adapted to indicate the number of available tests remaining in the cartridge.

10. The bodily fluid sampling device of claim 1, wherein the sensor includes:

a light source/detector positioned remotely from the cassette;

a light transmission means coupled to the light source/detector, the transmission means being adapted to transmit light from the light source/detector onto the test media tape; and a light detection means coupled to the light source/detector, the detection means being adapted to receive reflected light from the test media tape and transmit the reflected light to the light source/detector for analysis.

11. A test cassette for collecting a bodily fluid sample, comprising:

a test media tape having a contaminated section that is contaminated with past samples of the bodily fluid and an uncontaminated section;

a cover including a supply portion in which the uncontaminated section of the test media tape is enclosed, the cover further including a storage portion in which the contaminated section of the test media tape is enclosed, the cover defining an exposure opening along the test media tape at which the test media tape is exposed to the bodily fluid;

a supply reel disposed in the supply portion of the cover around which the uncontaminated section of the test media tape is wrapped;

a storage reel disposed in the storage portion of the cover around which the contaminated section of the test media tape is wrapped; and wherein the test media tape has a cover tape sealing the uncontaminated section of the test media tape.

12. The cassette of claim 11, wherein the cover defines a separate test opening at which the bodily fluid is tested.

13. The cassette of claim 12, wherein the test opening is positioned on an opposite side of the cover from the exposure opening, and the test opening is aligned with the exposure opening.

14. The cassette of claim 11, further comprising a cover reel attached to the cover tape, the cover reel being adapted to peel the cover tape from the test media tape.

15. The cassette of claim 11, wherein:

the test media tape includes a plurality of test sections;

each of the test sections includes a blister pack covering a test pad;

the blister pack being adapted to draw the bodily fluid up to the test pad; and the test media tape defining a piercing device throughway between adjacent pairs of the test sections.

16. The cassette of claim 11, wherein:

the test media tape defines a vacuum passageway;

the test media tape includes a seal membrane adapted to seal around a piercing device; and the test media tape includes a test pad positioned between the vacuum passageway and the seal membrane for collecting the bodily fluid.

17. A bodily fluid sampling device for analyzing a bodily fluid, comprising:
a test media cassette including
a test media tape adapted to collect the bodily fluid,
a supply portion storing an uncontaminated section of the test media tape that is uncontaminated with the bodily fluid,
a storage portion storing a contaminated section of the test media tape that is contaminated with the bodily fluid, and
an exposure portion positioned between the supply portion and the storage portion, the exposure portion being adapted to expose a section of the test media tape to the bodily fluid;
a sensor positioned between the supply portion and the storage portion to sense at least one property of the bodily fluid collected on the test media tape at the exposure portion of the cassette;
wherein the supply portion includes a supply reel, wherein the uncontaminated section of the test media tape is wound on the supply reel;
wherein the storage portion includes a storage reel, wherein the contaminated section of the test media tape is wound on the storage reel; and
wherein the test media tape includes a cover tape to preserve the test media tape; and
a cover reel attached to the cover tape, the cover reel being adapted to peel the cover tape from the test media tape before exposure to the bodily fluid.

18. A bodily fluid sampling device for analyzing a bodily fluid, comprising:
a test media cassette including
a test media tape adapted to collect the bodily fluid,
a supply portion storing an uncontaminated section of the test media tape that is uncontaminated with the bodily fluid,
a storage portion storing a contaminated section of the test media tape that is contaminated with the bodily fluid,
an exposure portion positioned between the supply portion and the storage portion, the exposure portion being adapted to expose a section of the test media tape to the bodily fluid;
a sensor positioned between the supply portion and the storage portion to sense at least one property of the bodily fluid collected on the test media tape at the exposure portion of the cassette;
a vacuum assembly to generate a vacuum;
a piercing device adapted to pierce skin and draw the bodily fluid;
wherein the test media tape includes separate test sections, each test section including a vacuum passageway defined in the test media and a seal membrane, the seal membrane being adapted to be pierced and seal around the piercing device when the bodily fluid is collected, each test section further including a test pad positioned between the vacuum passageway and the seal membrane, the test pad being adapted to collect the bodily fluid; and
wherein the vacuum assembly being adapted to form a vacuum in the vacuum cavity to draw the bodily fluid up the piercing device and onto the test pad during testing.

19. A bodily fluid sampling device for analyzing a bodily fluid, comprising:
a test media cassette including
a test media tape adapted to collect the bodily fluid,
a supply portion storing an uncontaminated section of the test media tape that is uncontaminated with the bodily fluid,
a storage portion storing a contaminated section of the test media tape that is contaminated with the bodily fluid,
an exposure portion positioned between the supply portion and the storage portion, the exposure portion being adapted to expose a section of the test media tape to the bodily fluid;
a sensor positioned between the supply portion and the storage portion to sense at least one property of the bodily fluid collected on the test media tape at the exposure portion of the cassette;
a piercing device mounted on a first pivotal arm to pierce skin; and
wherein the cassette is coupled to a second pivotal arm to pivot the cassette into position to collect the bodily fluid after the piercing device pierces the skin.

20. A bodily fluid sampling device for analyzing a bodily fluid, comprising:
a test media cassette including
a test media tape adapted to collect the bodily fluid,
a supply portion storing an uncontaminated section of the test media tape that is uncontaminated with the bodily fluid,
a storage portion storing a contaminated section of the test media tape that is contaminated with the bodily fluid,
an exposure portion positioned between the supply portion and the storage portion, the exposure portion being adapted to expose a section of the test media tape to the bodily fluid;
a sensor positioned between the supply portion and the storage portion to sense at least one property of the bodily fluid collected on the test media tape at the exposure portion of the cassette;
a piercing device to pierce skin;
an advancement mechanism to advance the test media tape in response to piercing of the skin by the piercing device;
the storage portion includes a storage reel and the contaminated section of the test media tape is wound on the storage reel; and
the advancement mechanism includes
a movable cover surrounding the piercing device, the movable cover being adapted to move and expose the piercing device during sampling, and
a rack member coupled between the movable cover and the storage reel to rotate the storage reel upon movement of the movable cover.

21. A test cassette for collecting a bodily fluid sample, comprising:
a test media tape having a contaminated section that is contaminated with past samples of the bodily fluid and an uncontaminated section;
a cover including a supply portion in which the uncontaminated section of the test media tape is enclosed, the cover further including a storage portion in which the contaminated section of the test media tape is enclosed, the cover defining an exposure opening along the test media tape at which the test media tape is exposed to the bodily fluid;

a supply reel disposed in the supply portion of the cover around which the uncontaminated section of the test media tape is wrapped;

a storage reel disposed in the storage portion of the cover around which the contaminated section of the test media tape is wrapped;

wherein the test media tape includes a plurality of test sections;

wherein each of the test sections includes a blister pack covering a test pad;

wherein the blister pack being adapted to draw the bodily fluid up to the test pad; and wherein the test media tape defining a piercing device throughway between adjacent pairs of the test sections.

22. A test cassette for collecting a bodily fluid sample, comprising:

a test media tape having a contaminated section that is contaminated with past samples of the bodily fluid and an uncontaminated section;

a cover including a supply portion in which the uncontaminated section of the test media tape is enclosed, the cover further including a storage portion in which the contaminated section of the test media tape is enclosed, the cover defining an exposure opening along the test media tape at which the test media tape is exposed to the bodily fluid;

a supply reel disposed in the supply portion of the cover around which the uncontaminated section of the test media tape is wrapped;

a storage reel disposed in the storage portion of the cover around which the contaminated section of the test media tape is wrapped;

wherein the test media tape defines a vacuum passageway;

wherein the test media tape includes a seal membrane adapted to seal around a piercing device; and wherein the test media tape includes a test pad positioned between the vacuum passageway and the seal membrane for collecting the bodily fluid.

23. A test cassette, comprising:

a test tape configured to analyze more than one body fluid sample;

a cover tape covering the test tape to protect the test tape prior to use; and means for peeling the cover tape from the test tape.

24. The test cassette of claim 23, wherein the means for peeling the cover tape includes a cover reel around which the cover tape is wound.

25. The test cassette of claim 23, further comprising:

a supply reel around which the test tape is wound prior to use; and a take-up reel around which the test tape is wound after use.

26. A test media cassette for analyzing a bodily fluid, comprising:

a test media tape adapted to analyze the bodily fluid;

a supply portion storing an uncontaminated section of the test media tape that is uncontaminated with the bodily fluid;

a storage portion storing a contaminated section of the test media tape that is contaminated with the bodily fluid; and wherein the test media tape includes a plurality of blister packs each having a raised surface with an opening for drawing the bodily fluid to the test media tape through capillary action.

27. The test media cassette of claim 26, further comprising a cutting device for creating the opening in the blister packs to draw the bodily fluid.

28. A bodily fluid sampling device, comprising:

a piercing device to form an incision in tissue;

a test media cassette including a test media tape adapted to analyze body fluid from the incision, a supply portion storing an uncontaminated section of the test media tape that is uncontaminated with the body fluid, and a storage portion storing a contaminated section of the test media tape that is contaminated with the body fluid;

an advancement mechanism configured to advance the contaminated section of the test media tape into the storage portion in response to piercing of the skin by the piercing device.

29. The bodily fluid sampling device of claim 28, wherein the advancement mechanism includes:

a movable cover surrounding the piercing device, the movable cover being adapted to move and expose the piercing device during sampling; and a rack member coupled between the movable cover and the storage reel to rotate the storage real upon movement of the movable cover.

* * * * *

UNITED STATES PATENT AND TRADEMARK OFFICE
CERTIFICATE OF CORRECTION

PATENT NO. : 6,988,996 B2
DATED : January 24, 2006
INVENTOR(S) : Roe et al.

It is certified that error appears in the above-identified patent and that said Letters Patent is hereby corrected as shown below:

<u>Title page,</u>
Item [56], References Cited, FOREIGN PATENT DOCUMENTS, insert
-- DE   42 34 553  A1     4/1993
   DE   198 19 407 A1    11/1999
   DE   198 49 539 A1     5/2000 --.

<u>Column 13,</u>
Lines 33, 50 and 57, change "a piercing device" to -- the piercing device --.
Line 37, change "the test media and" to -- the test media tape and --.
Line 45, change "the vacuum cavity" to -- a vacuum cavity --.

<u>Column 14,</u>
Line 6, change "the storage real" to -- the storage reel --.
Line 10, change "the cartridge" to -- the cassette --.

<u>Column 18,</u>
Line 47, change "the storage reel to rotate the storage reel" to -- the storage portion to rotate the storage portion --.

Signed and Sealed this

Ninth Day of May, 2006

JON W. DUDAS
*Director of the United States Patent and Trademark Office*